United States Patent [19]

Sands

[11] Patent Number: 5,716,961

[45] Date of Patent: Feb. 10, 1998

[54] TREATMENT OF TINNITUS USING NEUROPROTECTIVE AGENTS

[75] Inventor: Steven B. Sands, Stonington, Conn.

[73] Assignee: Pfizer Inc., New York, N.Y.

[21] Appl. No.: 709,996

[22] Filed: Sep. 9, 1996

Related U.S. Application Data

[60] Provisional application No. 60/003,855, Sep. 15, 1995.

[51] Int. Cl.⁶ .................. A61K 31/435; A61K 31/44; A61K 31/40

[52] U.S. Cl. .................. 514/277; 514/305; 514/429

[58] Field of Search ................ 514/277, 305, 514/429

[56] References Cited

PUBLICATIONS

Chemical Abstracts 119:95538 (1992).

Primary Examiner—Zohreh Fay
Attorney, Agent, or Firm—Peter C. Richardson; Paul H. Ginsburg; Bryan C. Zielinski

[57] ABSTRACT

A method of treating tinnitus in a mammal in need of such treatment, in which the method comprises administering a therapeutically effective amount of a compound of the formula

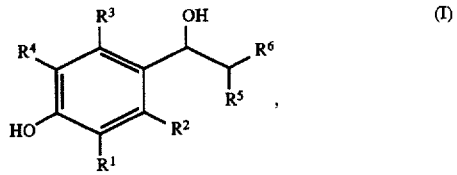

or a pharmaceutically acceptable salt thereof, wherein $R^1$–$R^6$ are as defined herein.

10 Claims, No Drawings

TREATMENT OF TINNITUS USING NEUROPROTECTIVE AGENTS

BACKGROUND OF THE INVENTION

This application is based on U.S. provisional application number 60/003,855, which was filed on Sep. 15, 1995.

The present invention relates to the treatment of tinnitus using neuroprotective agents defined by formula I below. The compounds of formula I are described in U.S. Pat. Nos. 5,185,343, 5,272,160, 5,338,754, and 5,356,905 (which issued, respectively, on Feb. 9, 1993; Dec. 21, 1993; Aug. 16, 1994; and Oct. 18, 1994); U.S. patent application Ser. Nos. 08/292,651 (filed Aug. 18, 1994) and 08/189,479 (filed Jan. 31, 1994); PCT International Application No. PCT/IB95/00398 which designates the United States (filed May 26, 1995); U.S. provisional patent application entitled "(1S, 2S)-1-(4-Hydroxyphenyl)-2-(4-Hydroxy-4-Phenylpiperidin-1-yl)-1-Propanol Methanesulfonate Trihydrate" (filed Aug. 11, 1995 in the name of M. M. Andino, T. G. Sinay, and E. F. Fiese); and United States provisional patent application entitled "Process For The Resolution Of Cis-Racemic 7-Benzyloxy-3-[4-(4-Fluorophenyl)-4-Hydroxy-Piperidin-1-yl]-Chroman-4-ol Dibenzoyl-D-Tartrate" (filed Jul. 20, 1995 in the name of M. Meltz et al.). All of the foregoing patents, United States patent applications and PCT international application are herein incorporated by reference in their entirety.

The NMDA receptor is a macromolecular complex consisting of an assembly of protein subunits that possess distinct binding sites that gate an ion channel permeable to sodium and calcium ions. Hansen and Krogsgaard-Larson, *Med. Res. Rev.*, 10, 55–94 (1990). There are binding sites for glutamic acid, glycine, and polyamines, and a site inside the ion channel where compounds such as phencyclidine (PCP) exert their antagonist effects.

The compounds of formula I are NMDA antagonists. NMDA antagonists are compounds that block the NMDA receptor by interacting with either the glutamate binding site or other sites on the receptor molecule. Examples of NMDA antagonists include D-2 amino 5-phosphonopentanoic acid (D-AP5), and D-2-amino-7-phosphonohaptanoic acid, Schoepp et al. *J. Neur. Transm.*, 85, 131–143 (1991). Antagonists of neurotransmission at NMDA receptors are useful therapeutic agents for the treatment of neurological disorders. J. Lehman, *The NMDA Receptor, Drugs of the Future*, 14(11), 1059 (1989). U.S. Pat. No. 4,902,695 is directed to series of competitive NMDA antagonists useful for the treatment of neurological disorders, including epilepsy, stroke, anxiety, cerebral ischemia, muscular spasms, and neurodegenerative disorders such as Alzheimer's disease and Huntington's disease. NMDA antagonists have also been reported to be effective for treating migraine (Canadian J. of Neurological Science, 19(4), 487 (1992)); drug addiction (Science, 251, 85 (1991)); and neuro-psychotic disorders related to AIDS (PIPS, 11, 1 (1990)).

The compounds defined by formula I below, and their pharmaceutically acceptable salts, are useful in the treatment of tinnitus by virtue of their selective neuroprotective activity. The condition known as tinnitus is typically described as a "ringing in the ears". Tinnitus is usually not itself a disease, but rather a secondary manifestation of disease (otosclerosis, Meniere's disease, tumors) or injury (drug-induced ototoxicity, head/ear trauma, exposure to loud noise) to the auditory system. Tinnitus occurs in varying degrees of severity, ranging from minor, sub-clinical annoyance to a severely disabling condition.

Tinnitus is very prevalent among adults. In a survey from Great Britain, about 10% of adults reported having prolonged, spontaneous tinnitus, with 1–3% reporting tinnitus severe enough to be disabling. A. C. Davis, International J. Epidemiology, 18, 911–917 (1989). The incidence in the United States is estimated to be 10–15% of adults have constant tinnitus, (up to 35% reporting transient episodes) with 0.1–1% of the population having a severe condition. J. W. P. Hazell (Ed.), *Tinnitus*, New York: Churchill Livingstone (1987). Severe tinnitus is disabling due to the psychological effect of "hearing" sounds or noise continuously. Tinnitus prevents concentration, disrupts or prevents sleep, and patients suffering with severe symptoms are frequently depressed. M. Sullivan et al., Archives of Internal Medicine, 153, 2251–2259 (1993).

A wide variety of agents have been used in attempts to treat tinnitus including intravenous administration of local anesthetics (lidocaine); trans-tympanic injections of local anesthetics; zinc, steroids, anticonvulsants (carbamazepine), tranquilizers (alprazolam), barbiturates, antidepressants (trimipramine, nortryptyline), and calcium channel blockers (flunarizine). The above listed therapies generally have shown limited efficacy. Although local anesthetics are effective, the route of administration (intravenous or trans-tympanic injection) is not acceptable. The only therapy that has some beneficial effect is alprazolam. In a study which germinated in anecdotes from patients receiving alprazolam for other conditions, patients reported that alprazolam (1–1.5 mg/day) provided some relief from symptoms in a 12 week trial, but there was not enough data to determine if alprazolam was acting peripherally to reduce or modify tinnitus in these patients. R. M. Johnson et al., Archives of Otolaryngology, Head and Neck Surgery, 119, 842–845 (1993). Alprazolam, however, carries with it problems associated with chronic use of benzodiazapines (sedation, addiction).

SUMMARY OF THE INVENTION

The present invention is directed to a method of treating tinnitus in a mammal in need of such treatment, comprising administering to said mammal a therapeutically effective amount of a compound of the formula

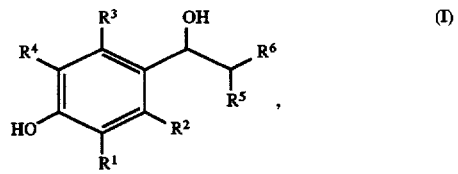

or a pharmaceutically acceptable salt thereof,
wherein:

(a) $R^2$ and $R^5$ are taken separately, $R^5$ is methyl or ethyl, and $R^1$, $R^2$, $R^3$ and $R^4$ are each independently selected from the group consisting of hydrogen, $C_1$–$C_6$ alkyl, halo, hydroxy, $CF_3$, and —$OR^7$; or, (b) $R^2$ and $R^5$ are taken together and are

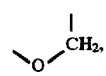

forming a chroman-4-ol ring, and $R^1$, $R^3$ and $R^4$ are each independently hydrogen, $C_1$–$C_6$ alkyl, halo, $CF_3$, OH or —$OR^7$; $R^6$ is

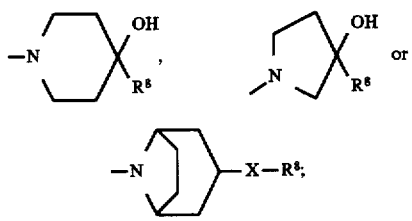

$R^7$ is methyl, ethyl, isopropyl or n-propyl; $R^8$ is phenyl optionally substituted with up to three substituents independently selected from the group consisting of $C_1$–$C_6$ alkyl, halo and $CF_3$; X is O, S and $(CH_2)_n$; and n is 0, 1, 2, or 3.

The invention is further directed to a pharmaceutical composition for treating tinnitus comprising a therapeutically effective amount of a compound of formula I, or a pharmaceutically acceptable salt thereof, and a pharmaceutically acceptable carrier.

With respect to the compounds of formula I, and their pharmaceutically acceptable salts, as used in accord with the present invention, it is to be understood that there are stereoisomeric forms such as optical and geometric isomers due to asymmetric carbon atoms and that the use of such isomers is also included within the scope of the invention.

The term "halo", as used herein, unless otherwise indicated, means a halogen atom such as fluorine, bromine, chlorine, or iodine.

The term "alkyl", as used herein, unless otherwise indicated, includes saturated monovalent hydrocarbon radicals having straight or branched moieties.

The phrase "treatment of tinnitus" as used herein, unless otherwise indicated, includes methods to cure, lessen or prevent tinnitus, regardless of its cause, in a mammal, such as a human. An example of preventing tinnitus would be the use of the compounds of formula I, or their pharmaceutically acceptable salts, prior to or during the use of certain cancer treatment drugs that are associated with drug-induced ototoxicity.

The phrase "therapeutically effective amount" as used herein, unless otherwise indicated, means an amount effective in the treatment of tinnitus, as defined above.

The phrase "pharmaceutically acceptable salt(s)", as used herein, unless otherwise indicated, means such salts as the hydrochloride, hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts.

Preferred compounds for use in the present invention include those of formula I wherein $R^2$ and $R^5$ are taken separately; $R^2$ and $R^3$ are hydrogen; $R^6$ is

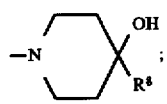

and $R^8$ is phenyl, 4-halophenyl or 4-trifluoromethylphenyl. Within this group, more specific preferred compounds are those wherein $R^5$ is methyl having a 1S*,2S* relative stereochemistry:

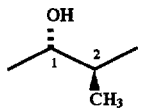

Other preferred compounds to be used in accord with the present invention compounds include those of formula I wherein $R^2$ and $R^5$ are taken together and are

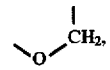

forming a chroman-4-ol ring. Within this group, preferred compounds also include those wherein the C-3 and C-4 positions of said chroman-4-ol ring have a 3R*,4S* relative stereochemistry:

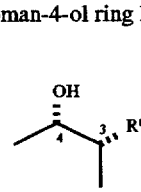

Within this group, preferred compounds also include those wherein $R^6$ is

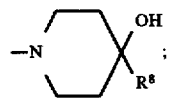

and $R^8$ is phenyl or 4-halophenyl.

Specific preferred compounds to be used in accord with the present invention include the following ere (3R,4S)-3-[4-(4-fluorophenyl)-4-hydroxy-piperidin-1-yl]-chroman-4,7-diol, (1S,2S)-1-(4-hydroxyphenyl)-2-(4-hydroxy-4-phenylpiperidin-1-yl)-1-propanol, and the pharmaceutically acceptable salts of both of the foregoing compounds.

Particularly preferred compounds to be used in accord with the present invention are (1S,2S)-1-(4-hydroxyphenyl)-2-(4-hydroxy-4-phenylpiperidin-1-yl)-1-propanol, the tartrate and mesylate salts of said compound, and trihydrate mesylate salt of said compound.

Other particularly preferred compounds to be used in accord with the present invention is (3R,4S)-3-[4-(4-fluorophenyl)-4-hydroxy-piperidin-1-yl]-chroman-4,7-diol, and the tartrate, lactate and mandelate salts of said compound.

DETAILED DESCRIPTION OF THE INVENTION

The compounds of formula I are readily prepared. The compounds of formula I wherein $R^2$ and $R^5$ are taken together forming a chroman-4-ol ring and $R_1$, $R^3$, and $R^4$ are hydrogen, can be prepared by one or more of the synthetic methods described and referred to in U.S. Pat. No. 5,356,905. The compounds of formula I wherein $R^2$ and $R^5$ are taken separately and $R^1$, $R^2$, $R^3$ and $R^4$ are hydrogen can be prepared by one or more of the synthetic methods described and referred to in U.S. Pat. Nos. 5,185,343, 5,272,160, and 5,338,754. The compounds of formula I can also be prepared by one or more of the synthetic methods described and referred to in U.S. patent application Ser. Nos. 08/292,651 and 08/189,479; United States provisional patent application entitled "(1S,2S)-1-(4-Hydroxyphenyl)-2-(4-Hydroxy-4-

Phenylpiperidin-1-yl)-1-Propanol Methanesulfonate Trihydrate"; PCT international application no. PCT/IB95/00398 which designates the U.S.; and United States provisional patent application entitled "Process For The Resolution Of Cis-Racemic 7-Benzyloxy-3-[4-(4-Fluorophenyl)-4-Hydroxy-Piperidin-1-yl]-Chroman-4-ol Dibenzoyl-D-Tartrate". The foregoing United States patents, United States applications and PCT international application are referred to above.

A preferred compound, (1S,2S)-1-(4-hydroxyphenyl)-2-(4-hydroxy-4-phenylpiperidin-1-yl)-1-propanol ((1S,2S) free base), and its tartrate salt, can be prepared as described in U.S. Pat. No. 5,272,160, referred to above. The resolution of racemic 1-(4-hydroxyphenyl)-2-(4-hydroxy-4-phenylpiperidin-1-yl)-1-propanol to form the (1S,2S) free base and the corresponding (1R,2R) enantiomer can be carried out as described in U.S. provisional patent application entitled "(1S,2S)-1-(4-Hydroxyphenyl)-2-(4-Hydroxy-4-Phenylpiperidin-3-yl)-1-Propanol Methanesulfonate Trihydrate", referred to above, and as exemplified in Example 1 below.

The anhydrous mesylate of the (1S,2S) free base can be prepared as described in U.S. Pat. No. 5,272,160, referred to above. The anhydrous mesylate of the (1S,2S) free base, when equilibrated in an 81% relative humidity environment, will convert to the mesylate salt trihydrate of the (1S,2S) enantiomer.

The mesylate salt trihydrate of (1S,2S)-1-(4-hydroxyphenyl)-2-(4-hydroxy-4-phenylpiperidin-1-yl)-1-propanol can be prepared from the (1S,2S) free base as described in United States provisional patent application entitled "(1S,2S)-1-(4-Hydroxyphenyl)-2-(4-Hydroxy-4-Phenylpiperidin-1-yl)-1-Propanol Methanesulfonate Trihydrate", referred to above. In this method, (1S,2S) free base is dissolved in water at 30° C. To this solution is added at least 1 equivalent of methane sulfonic acid and the resulting mixture is warmed to 60°–65° C. The warm solution can be filtered to render it particulate free. The solution is concentrated to approximately 40% of the initial volume, cooled below 10° C., isolated by filtration and dried to a water content (measured Karl Fischer titration) of approximately 11.3%. The resulting crystalline mesylate salt trihydrate can be further purified by recrystallization.

Another preferred compound, (3R,4S)-3-[4-(4-fluorophenyl)-4-hydroxy-piperidin-1-yl]-chroman-4,7-diol ((3R,4S) chromanol), can be prepared as described in U.S. Pat. No. 5,356,905, U.S. patent application Ser. No. 08/189,479, and United States provisional patent application entitled "Process For The Resolution Of Cis-Racemic 7-Benzyloxy-3-[4-(4-Fluorophenyl)-4-Hydroxy-Piperidin-1-yl]-Chroman-4-ol Dibenzoyl-D-Tartrate", all three of which are referred to above. The starting materials and reagents required for the synthesis of the (3R,4S) chromanol are readily available, either commercially, according to synthetic methods disclosed in the literature, or by synthetic methods exemplified in the description provided below.

The (3R,4S) chromanol can be prepared by fractional crystallization of the L-proline ester of racemic cis-7-benzyloxy-3-[4-(4-fluorophenyl)-4-hydroxy-piperidin-1-yl]-chroman-4-ol, as described in U.S. patent application Ser. No. 08/189,479, referred to above. In a preferred method, the resolution method described in United States provisional patent application entitled "Process For The Resolution Of Cis-Racemic 7-Benzyloxy-3-[4-(4-fluorophenyl)-4-Hydroxy-Piperidin-1-yl]-Chroman-4-ol Dibenzoyl-D-Tartrate", referred to above, and as exemplified in Example 3. In this method, the parent chromanol is prepared by dissolving racemic cis-7-benzyloxy-3-[4-(4-fluorophenyl)-4-hydroxy-piperidin-1-yl]-chroman-4-ol with an equal molar amount of dibenzoyl-D-tartaric acid in boiling aqueous ethanol. Racemic cis-7-benzyloxy-3-[4-(4-fluorophenyl)-4-hydroxy-piperidin-1-yl]-chroman-4-ol is prepared as described in U.S. patent application Ser. No. 08/189,479, referred to above. The concentration of aqueous ethanol is not critical and may be varied between 75% and 9.5% ethanol (ETOH). A concentration of 9:1/ETOH:$H_2O$ has been found to be effective and is preferred. A sufficient amount of the aqueous ethanol solvent to dissolve the racemic compound is required. This amount has been found to be about 17 ml per gram of racemic compound.

Upon stirring while heating under reflux, the racemic compound dissolves to form a hazy solution which is allowed to cool with stirring whereupon the (+) isomer, (3R,4S)-7-benzyloxy-3-[4-(4-fluorophenyl)-4-hydroxy-piperidin-yl]-chroman-4-ol dibenzoyl-D-tartrate, precipitates and may be collected by filtration and washed with aqueous ethanol. This is the tartrate salt of the (3R,4S) chromanol. The lactate and mandelate salts of the (3R,4S) chromanol are prepared in an analogous manner. This initial product is of about 90% optical purity. If a higher purity is desired, the product may be heated again with aqueous ethanol, cooled and the product collected and washed. Two such treatments were found to yield the (+) isomer of 99.4% optical purity in an overall yield of 74%. This procedure is preferred over the procedure described in U.S. patent application Ser. No. 08/189,479, referred to above, in that it avoids a reduction step with lithium aluminum hydride and is therefore more suitable for bulk operations. This procedure also produces a significantly higher yield of the desired product.

The above described (+) isomer can be converted to (3R,4S)-3-[4-(4-fluorophenyl)-4-hydroxy-piperidin-1-yl]-chroman-4,7-diol by standard procedures. For example, treatment with dilute base can be used to free the piperidinyl base and subsequent hydrogeneration removes the 7-benzyl group to yield the (3R,4S) chromanol.

In general, the pharmaceutically acceptable acid addition salts of the compounds of formula I can readily be prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The compounds of formula I, and their pharmaceutically acceptable salts, possess selective neuroprotective activity based upon their antiischemic activity and ability to block excitory amino acid receptors. The preferred procedure for evaluating the neuroprotective activity of this compound is that described by Ismail A. Shalaby, et al., in *J. Pharm. and Experimental Therapeutics*, 260, 925 (1992). This article is incorporated herein by reference in its entirety and is described below.

Cell culture.

Seventeen day fetal rat (CD, Charles River Breeding Laboratories, Inc., Wilmington, Mass.) hippocampal cells are cultured on PRIMARIA culture plates (Falcon Co., Lincoln Park, N.J.) for 2 to 3 weeks in serum containing culture medium (minimum essential medium with nonessential amino acids, containing 2 mM glutamine, 21 mM glucose, penicillin/streptomycin (5000 U each), 10% feted bovine serum (days 1–7) and 10% horse serum (days 1–21). Cells are either plated on 96-well microtiter plates at a density of 80,000 cells per well or on 24-well culture plates at a density of 250,000 cells per well. Cultures are grown at 37° C. in a humidified $CO_2$ tissue culture incubator containing 5% $CO_2$-95% air. Proliferation of nonneuronal cells is controlled by adding 20 µM uridine and 20 µM 5-fluoro-2-deoxyuridine (Sigma Chemical Co., St. Louis, Mo.) from days 6 to 8 of culture. Culture media is exchanged every 2 to 3 days with fresh stock.

Glutamate toxicity.

The cultures are assessed for glutamate toxicity 2 to 3 weeks from initial plating. Culture media is removed and cultures rinsed twice with a CSS (in millimolar:): NaCl, 12-; KCl, 5.4; $MgCl_2$, 0.8; $CaCl_2$, 1.8; glucose, 15; and 4-(2-hydroxyethyl)-1-piperazineethanesulfonic acid, 25 mM (pH 7.4). Cultures are then exposed for 15 min (37° C.) to various concentrations of glutamate. After this incubation, cultures are rinsed 3 times with glutamate-free CSS and twice with fresh culture medium without serum. The cultures are than incubated for 20 to 24 hr in serum-free culture medium. The compound being tested is added 2 min before and during the 15-min exposure to glutamate. In some experiments, the compound is added at different times after the glutamate exposure and for the following 20 to 24 hr.

Cell viability is routinely assessed 20 to 24 hours after the excitotoxin exposure by measuring the activity of the cytosolic enzyme LDH. LDH activity is determined from the culture medium of each of the 96 wells of the microtiter plates. A 50-µl sample of the media is added to an equal volume of sodium-phosphate buffer (0.1M, pH 7.4) containing 1.32 mM sodium pyruvate and 2.9 mM NADH. The 340 nm absorbance of the total reaction mixture for each of the 96 wells is monitored every 5 sec for 2 min by an automated spectrophotometric microtiter plate reader (Molecular Devices; Menlo Park, Calif.). The rate of absorbance is automatically calculated using an IBM SOFTmax program (version 1.01; Molecular Devices) and is used as the index of LDH activity.

Morphological assessment of neuronal viability is determined using phrase contrast microscopy. The 96-well culture plates do not permit good phase-contrast imagery, so cells cultured on 24-well plates are used for this purpose. Quantitatively, both culture platings are equally sensitive to glutamate toxicity, and display 2- to 3-fold increases in LDH activity 24 hours after exposure to 0.1 to 1.0 mM glutamate.

Reagents.

DTG can be purchased from Aldrich Chemical Company (Milwaukee, Wis.), and haloperidol from Research Biochemicals Inc. (Natick, Mass.). Spermine can be purchased from Sigma Chemical Co. (St. Louis, Mo.). Horse and fetal bovine serum can be purchased from Hyclone (Logan, Utah). Culture medium, glutamine and penicillin/streptomycin can be purchased from Gibco Co. (Grand Island, N.Y.).

Data analysis.

Neurotoxicity can be quantified by measuring the activity of LDH present in the culture medium 20 to 24 hours after glutamate exposure. The increased LDH activity in the culture media correlates with destruction and degeneration of neurons (Koh and Choi, 1987). Because actual levels of LDH vary from different cultures, data are routinely expressed relative to buffer-treated sister wells of the same culture plate. To obtain an index of LDH activity from glutamate and drug-treated cultures, the LDH values from control cultures are subtracted from that of the treatment groups. Data for drug treatments is expressed as a percentage of the increase in LDH induced by 1 mM glutamate (or NMDA) for each experiment. Concentrations of NMDA antagonists required to reverse 50% of the LDH increase induced by excitotoxins ($IC_{50}$) are calculated using log-probit analysis from the pooled results of three independent experiments.

The neuroprotective activity of the compounds of formula I, and their pharmaceutically acceptable salts, render them useful in the treatment of tinnitus.

In the treatment of tinnitus using a compound of formula I, or a pharmaceutically acceptable salt thereof, the dosage is typically from about 0.02 to 20 mg/kg/day (0.001–1 g/day in a typical human weighing 50 kg) in single or divided doses, regardless of the route of administration. A more preferred dosage range is from about 0.15 mg/kg/day to about 20 mg/kg/day. Of course, depending upon the exact nature of the illness and the condition of the patient, doses outside this range may be prescribed by the attending physician. The oral route of administration is generally preferred. However, if the patient is unable to swallow, or oral absorption is otherwise impaired, another route of administration such as suppositories, or parenteral (i.m., i.v.) or topical administration will be appropriate.

The compounds of formula I, and their pharmaceutically acceptable salts, may be administered in the form of pharmaceutical compositions together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; and for topical administration, in the form of solutions, lotions, ointments, salves and the like.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

EXAMPLE 1

Enantiomeric (1S, 2S)- and (1R, 2R)-1-(4-Hydroxyphenyl)-2-(4-hydroxy-4-phenylpiperidin-1-yl)-1-propanols (+)-Tartaric acid (300 mg, 2 mmol) was dissolved in 30 mL warm methanol. Racemic 1S* , 2S*-1-(4- hydroxyphenyl)-2-(4-hydroxy-4-phenylpiperidin-1-yl)-1-propanol (655 mg, 2 mmol) was added all at once. With stirring and gentle warming a colorless homogeneous solution was obtained. Upon standing at ambient temperature 24 hours, 319 mg (66%) of a fluffy white precipitate was obtained. This product was recrystallized from methanol to give 263 mg of the (+)-tartrate salt of levorotatory title product as a white solid; mp 206.5°–207.5° C.; [alpha]$_D$=−36.2°. This salt (115 mg) was added to 50 mL of saturated NaHCO$_3$. Ethyl acetate (5 mL) was added and the mixture was vigorously stirred 30 minutes. The aqueous phase was repeatedly extracted with ethyl acetate. The organic layers were combined and washed with brine, dried over calcium sulfate, and concentrated. The tan residue was recrystallized from ethyl acetate-hexene to give 32 mg (39%) of white, levorotatory title product; mp 203°–204° C.; [alpha]$_D$=−56.9°. Anal. Calc'd. for C$_{20}$H$_{25}$NO$_3$: C, 73.37; H, 7.70; N, 4.28. Found: C, 72.61; H, 7.45; N, 4.21.

The filtrate from the (+)-tartrate salt preparation above was treated with 100 mL saturated aqueous NaHCO$_3$ and extracted well with ethyl acetate. The combined organic extracts were washed with brine, dried over calcium sulfate and concentrated to give 380 mg of recovered starting material (partially resolved). This material was treated with (−)-tartaric acid (174 mg) in 30 mL of methanol as above. After standing for 24 hours, filtration gave 320 mg (66%) of product which was further recrystallized from methanol to produce 239 mg of the (−)-tartrate salt of dextrorotatory title product; mp 206.5°–207.5° C. [alpha]$_D$=+33.9°. The latter was converted to dextrorotatory title product in the manner above in 49% yield; mp 204°–205° C.; [alpha]$_D$=+58.4°. Anal. Found: C, 72.94; H, 7.64; N, 4.24.

EXAMPLE 2

(1S, 2S)-1-(4-hydroxyphenyl)-2-(4-hydroxy-4-phenylpiperidin-yl)-1-propanol Methanesulfonate Trihydrate

STEP 1

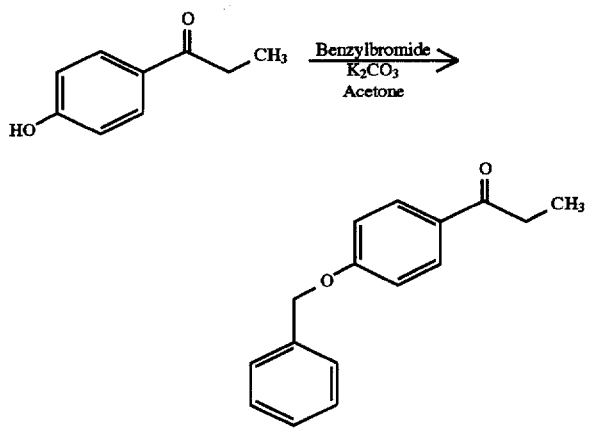

A 50 gallon glass lined reactor was charged with 17.1 gallons of acetone, 8.65 kilograms (kg) (57.7 mol) of 4'-hydroxypropiophenone, 9.95 kg (72.0 mol) of potassium carbonate and 6.8 liters (l) (57.7 mol) of benzylbromide. The mixture was heated to reflux (56° C.) for 20 hours. Analysis of thin layer chromatography (TLC) revealed that the reaction was essentially complete. The suspension was atmospherically concentrated to a volume of 10 gallons and 17.1 gallons of water were charged. The suspension was granulated at 25° C. for 1 hour. The product was filtered on a 30" Lapp and washed with 4.6 gallons of water followed by a mixture of 6.9 gallons of hexane and 2.3 gallons of isopropanol. After vacuum drying at 45° C., this yielded 13.35 kg (95.4%) of the above-depicted product.

A second run was carried out with 9.8 kg (65.25 mol) of 4'-hydroxypropiophenone using the procedure described above. After drying 15.1 kg (96.3%) of the above-depicted product was obtained.

STEP 2

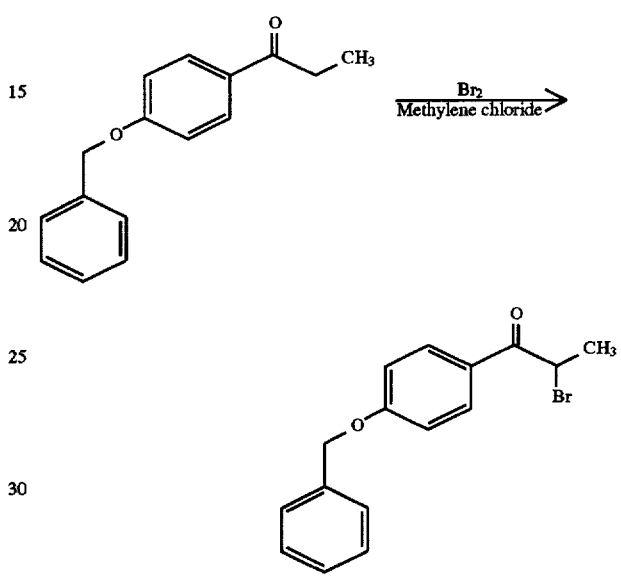

Under a nitrogen atmosphere, a 100 gallon glass lined reactor was charged with 75 gallons of methylene chloride and 28.2 kg (117.5 mol) of the product from step 1. The solution was stirred five minutes and then 18.8 kg of bromine was charged. The reaction was stirred for 0.5 hours at 22° C. Analysis of TLC revealed that the reaction was essentially complete. To the solution was charged 37 gallons of water and the mixture was stirred for 15 minutes. The methylene chloride was separated and washed with 18.5 gallons of saturated aqueous sodium bicarbonate. The methylene chloride was separated, atmospherically concentrated to a volume of 40 gallons and 60 gallons of isopropanol was charged. The concentration was continued until a pot temperature of 80° C. and final volume of 40 gallons were obtained. The suspension was cooled to 20° C. and granulated for 18 hours. The product was filtered on a 30" Lapp and washed with 10 gallons of isopropanol. After vacuum drying at 45° C., this yielded 29.1 kg (77.6%) of the above-depicted product.

STEP 3

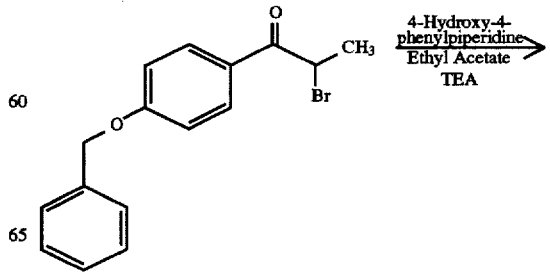

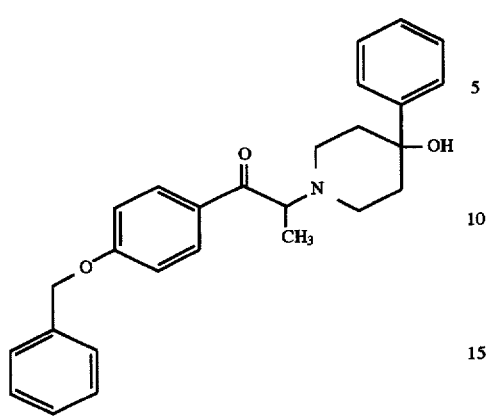

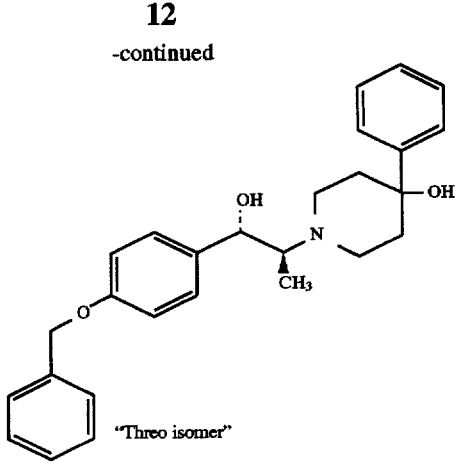

"Threo isomer"

Under a nitrogen atmosphere, a 20 gallon glass lined reactor was charged with 4.90 kg (15.3 mol) of the product from step 2, 7.0 gallons of ethyl acetate, 2.70 kg (15.3 mol) of 4-hydroxy-4-phenylpiperidine and 1.54 kg of triethylamine (15.3 mol). The solution was heated to reflux (77° C.) for 18 hours. The resulting suspension was cooled to 20° C. Analysis by TLC revealed that the reaction was essentially complete. The byproduct (triethylamine hydrobromide salt) was filtered on a 30" Lapp and washed with 4 gallons of ethyl acetate. The filtrate was concentrated under vacuum to a volume of 17 liters. The concentrate was charged to 48 liters of hexane and the resulting suspension granulated for 2 hours at 20° C. The product was filtered on a 30" Lapp and washed with 4 gallons of hexane. After vacuum drying at 50° C., this yielded 4.9 kg (77%) of the above-depicted product.

A second run was carried out with 3.6 kg (11.3 mol) of the product from step 2 using the procedure described above. After drying 4.1 kg (87%) of the above-depicted product was obtained.

STEP 4

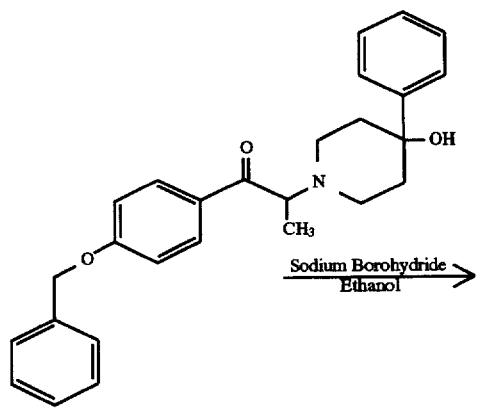

Under a nitrogen atmosphere, a 100 gallon glass lined reactor was charged with 87.0 gallons of 2B ethanol and 1.7 kg (45.2 mol) of sodium borohydride. The resulting solution was stirred at 25° C. and 9.4 kg (22.6 mol) of the product from step 3 was charged. The suspension was stirred for 18 hours at 25°–30° C. Analysis by TLC revealed that the reaction was essentially complete to the desired threo diastereoisomer. To the suspension was charged 7.8 liters of water. The suspension was concentrated under vacuum to a volume of 40 gallons. After granulating for 1 hour, the product was filtered on a 30" Lapp and washed with 2 gallons of 2B ethanol. The wet product, 9.4 gallons of 2B-ethanol and 8.7 gallons of water were charged to a 100 gallon glass lined reactor. The suspension was stirred at reflux (78° C.) for 16 hours. The suspension was cooled to 25° C., filtered on 30" Lapp and washed with 7 gallons of water followed by 4 gallons of 2B ethanol. After air drying at 50° C., this yielded 8.2 kg (86.5%) of the above-depicted product. This material was recrystallized in the following manner.

A 100 gallon glass lined reactor was charged with 7.9 kg (18.9 mol) of the product from step 3, 20 gallons of 2B ethanol and 4 gallons of acetone. The suspension was heated to 70° C. producing a solution. The solution was concentrated atmospherically to a volume of 15 gallons. The suspension was cooled to 25° C. and granulated for 1 hour. The product was filtered on a 30" Lapp. The wet product and 11.7 gallons of 2B ethanol was charged to a 100 gallon glass lined reactor. The suspension was heated to reflux (78° C.) for 18 hours. The suspension was cooled to 25° C., filtered on a 30" Lapp and washed with 2 gallons of 2B ethanol. After air drying at 50° C. this yielded 5.6 kg (70.6%) of the above-depicted product.

STEP 5

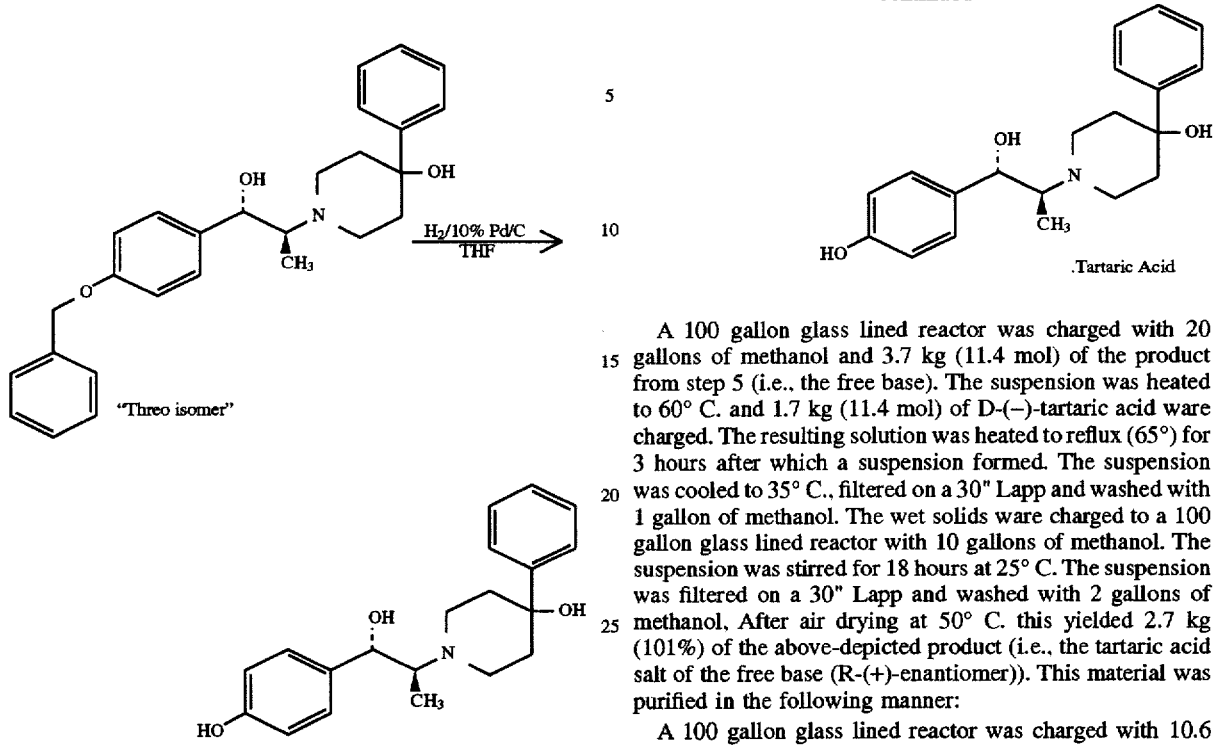

Under a nitrogen atmosphere, a 50 gallon glass lined reactor was charged with 825 g of 10% palladium on carbon (50% water wet), 5.5 kg (13.2 mol) of the product from step 4 and 15.5 gallons of tetrahydrofuran (THF). The mixture was hydrogenated between 40°–50° C. for 2 hours. At this time, analysis by TLC revealed that the reduction was essentially complete. The reaction was filtered through a 14" sparkler precoated with Celite and washed with 8 gallons of THF. The filtrate was transferred to a clean 100 gallon glass lined reactor, vacuum concentrated to a volume of 7 gallons and 21 gallons of ethyl acetate were charged. The suspension was atmospherically concentrated to a volume of 10 gallons and a pot temperature of 72° C. The suspension was cooled to 10° C., filtered on a 30" Lapp and washed with 2 gallons of ethyl acetate. After air drying at 55° C. this yielded a 3.9 kg (90%) of the above-depicted product (i.e., the free base).

STEP 6

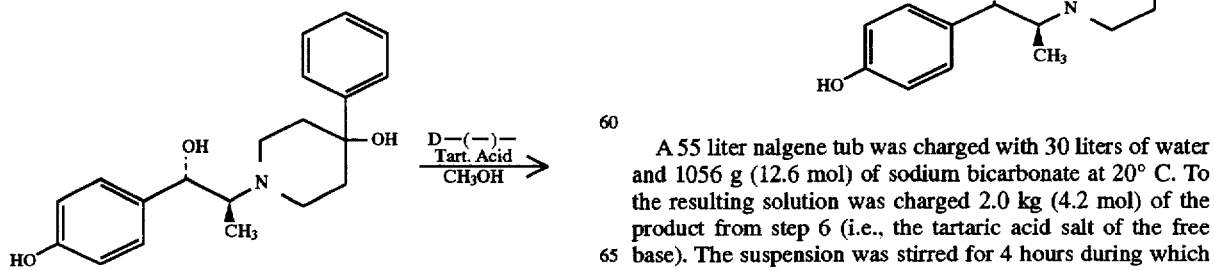

A 100 gallon glass lined reactor was charged with 20 gallons of methanol and 3.7 kg (11.4 mol) of the product from step 5 (i.e., the free base). The suspension was heated to 60° C. and 1.7 kg (11.4 mol) of D-(−)-tartaric acid ware charged. The resulting solution was heated to reflux (65°) for 3 hours after which a suspension formed. The suspension was cooled to 35° C., filtered on a 30" Lapp and washed with 1 gallon of methanol. The wet solids ware charged to a 100 gallon glass lined reactor with 10 gallons of methanol. The suspension was stirred for 18 hours at 25° C. The suspension was filtered on a 30" Lapp and washed with 2 gallons of methanol. After air drying at 50° C. this yielded 2.7 kg (101%) of the above-depicted product (i.e., the tartaric acid salt of the free base (R-(+)-enantiomer)). This material was purified in the following manner:

A 100 gallon glass lined reactor was charged with 10.6 gallons of methanol and 2.67 kg (5.6 mol) of the above tartaric acid salt. The suspension was heated to reflux (80° C.) for 18 hours. The suspension was cooled to 30° C., filtered on a 30" Lapp and washed with 4 gallons of methanol. After air drying at 50° C., this yielded 2.05 kg (76.7%) of the above-depicted product (i.e., the tartaric acid salt of the free base).

STEP 7

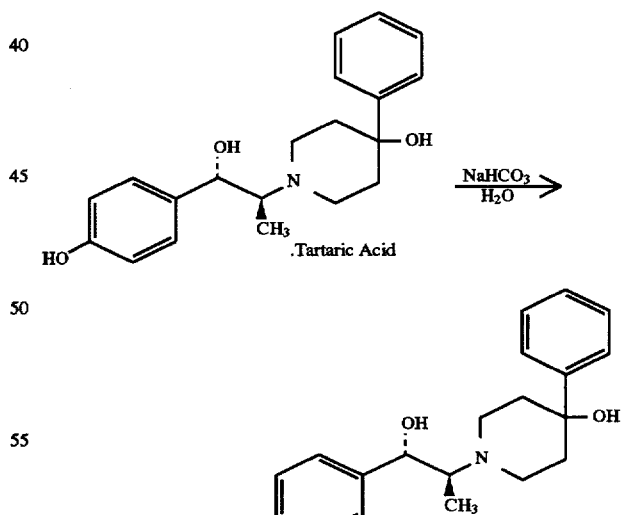

A 55 liter nalgene tub was charged with 30 liters of water and 1056 g (12.6 mol) of sodium bicarbonate at 20° C. To the resulting solution was charged 2.0 kg (4.2 mol) of the product from step 6 (i.e., the tartaric acid salt of the free base). The suspension was stirred for 4 hours during which a great deal foaming occurred. After the foaming ceased, the suspension was filtered on a 32 cm funnel and washed with 1 gallon of water. After air drying at 50° C., this yielded 1.28 kg (93.5%) of the above-depicted product (i.e., the free base).

STEP 8

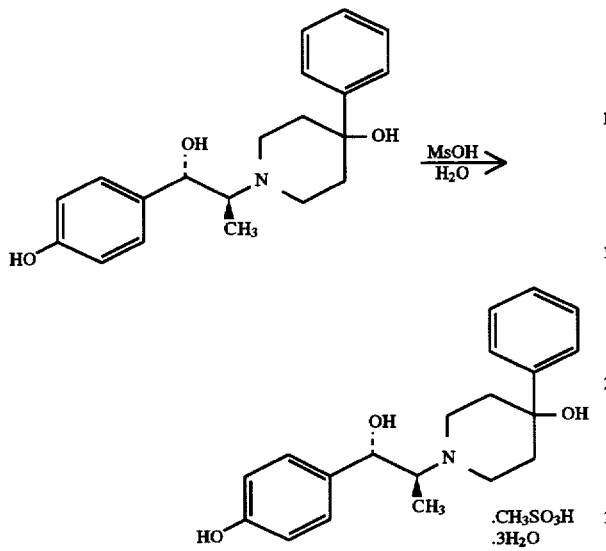

A 22 liter flask was charged with 1277 g (3.9 mol) of product from step 7 and 14 liters of water. The suspension was warmed to 30° C. and 375 g (3.9 mol) of methane sulfonic acid were charged. The resulting solution was warmed to 60° C., clarified by filtering through diatomaceous earth (Celite®) and washed with 2 liters of water. The speck-free filtrate was concentrated under vacuum to a volume of 6 liters. The suspension was cooled to 0°–5° C. and granulated for 1 hour. The product was filtered on a 18" filter funnel and washed with 635 ml of speck-free water. After air drying at 25° C. for 18 hours, this yielded 1646 g (88%) of the above-depicted product (i.e., the mesylate salt trihydrate).

EXAMPLE 3

3R 4S -7-Benzyloxy-3-[4-4-fluorophenyl-4-hydroxy-piperidin-yl]-chroman-4-ol dibenzoyl-D-tartrate A. Racemic cis-7-benzyloxy-3-[4-(4-fluorophenyl)-4-hydroxy-piperidin-1-yl]-chroman-4-ol (2.07 g, 4.6 mmol) and dibenzoyl-D-tartaric acid (1.65 g, 4.6 mmol) were suspended in 30 ml, 90% ethanol/water. The resulting mixture was stirred and heated to reflux; an additional 5 ml, 90% ethanol/water was added and a hazy solution was obtained. The resulting solution was stirred overnight at room temperature. The solid which formed was collected by filtration and washed twice with 3 ml, 95% ethanol to yield 1.55 g (83.4%) of the title product which was shown to be of 87% purity by HPLC.

B. The above product (1.2 g) was suspended in 21.4 ml of 90% EtOH:H$_2$O, stirred and heated under reflux for 1.5 hours and then cooled to room temperature. The solid product was collected by filtration and washed with two 3 ml portions of 90% ETOH:H$_2$O. The yield was 1.1 g of 98.0% optical purity.

C. The procedure of step B was repeated with the product of step B yielding 97% of a product which had 99.4% optical purity.

Optical purity was determined by HPLC using a 250×4.6 mm Chiralpak® AD column (Chiral Technologies, Exton, Pa.) with the mobile phase comprising 600 ml hexane, 400 ml isopropanol, 1 ml trifluoroacetic acid and 0.5 ml diethylamine. The flow rate was 0.7 ml/min with an injection volume of 20 μl containing 0.1 to 0.4 mg sample/ml. Detection was set for 220 nm.

I claim:

1. A method of treating tinnitus in a mammal comprising administering to a mammal in need of such treatment a therapeutically effective amount of a compound of the formula

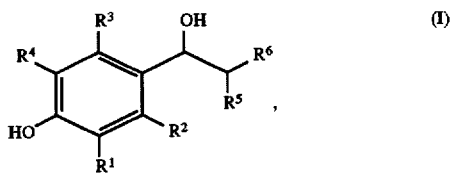

or a pharmaceutically acceptable salt thereof, wherein: (a) R$^2$ and R$^5$ are taken separately and R$^1$, R$^2$, R$^3$ and R$^4$ are each independently hydrogen, C$_1$–C$_6$ alkyl, halo, CF$_3$, OH or —OR$^7$ and R$^5$ is methyl or ethyl; or (b) R$^2$ and R$^5$ are taken together and are

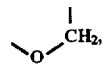

forming a chroman-4-ol ring, and R$^1$, R$^3$ and R$^4$ are each independently hydrogen, C$_1$–C$_6$ alkyl, halo, CF$_3$, OH or —OR$^7$; R$^6$ is

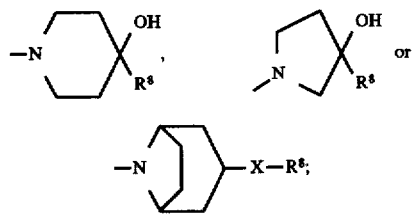

R$^7$ is methyl, ethyl, isopropyl or n-propyl; R$^8$ is phenyl optionally substituted with up to three substituents independently selected from the group consisting of (C$_1$–C$_6$) alkyl, halo or CF$_3$; X is O, S and (CH$_2$)$_n$; and n is 0, 1, 2, or 3.

2. The method of claim 1 wherein R$^2$ and R$^5$ are taken separately; R$^2$ and R$^3$ are hydrogen; R$^6$ is

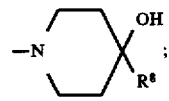

and R$^8$ is phenyl, 4-halophenyl or 4-trifluoromethylphenyl.

3. The method of claim 2 wherein R$^5$ is methyl having a 1S*,2S* relative stereochemistry:

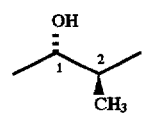

4. The method of claim 1 wherein R$^2$ and R$^5$ are taken together and are

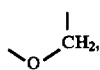

forming a chroman-4-ol ring.

5. The method of claim 4 wherein the C-3 and C-4 positions of said chroman-4-ol ring have a 3R*,4S* relative stereochemistry:

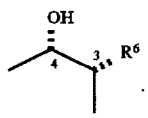

6. The method of claim 5 wherein $R^6$ is

and $R^8$ is phenyl or 4-halophenyl.

7. The method of claim 1 wherein said compound is selected from the group consisting of (3R,4S)-3-[4-(4-fluorophenyl)-4-hydroxy-piperidin-1-yl]-chroman-4,7-diol, (1S,2S)-1-(4-hydroxyphenyl)-2-(4-hydroxy-4-phenylpiperidin-1-yl)-1-propanol, and the pharmaceutically acceptable salts of both of said compounds.

8. The method of claim 7 wherein said compound is (1S,2S)-1-(4-hydroxyphenyl)-2-(4-hydroxy-4-phenylpiperidin-1-yl)-1-propanol, the tartrate salt of said compound, or the mesylate salt of said compound.

9. The method of claim 7 wherein said compound is the trihydrate mesylate salt of (1S,2S)-1-(4-hydroxyphenyl)-2-(4-hydroxy-4-phenylpiperidin-1-yl)-1-propanol.

10. The method of claim 7 wherein said compound is selected from the group consisting of (3R,4S)-3-[4-(4-fluorophenyl)-4-hydroxy-piperidin-1-yl]-chroman-4,7-diol, and the tartrate, lactate, and mandelate salts of said compound.

* * * * *